United States Patent [19]

Rogers et al.

[11] Patent Number: 5,702,252
[45] Date of Patent: Dec. 30, 1997

[54] THERMALLY STABILIZED CASTING CORE

[75] Inventors: Dan Paul Rogers, Royal Palm Beach, Fla.; Edward Freer Smith, III, Madison, Conn.

[73] Assignee: Implant Innovations, Inc., Palm Beach Gardens, Fla.

[21] Appl. No.: 396,758

[22] Filed: Mar. 1, 1995

[51] Int. Cl.[6] .................................................. A61C 8/00
[52] U.S. Cl. .................................................. 433/173
[58] Field of Search .................................. 433/172, 173, 433/174, 175, 176

[56] References Cited

U.S. PATENT DOCUMENTS

| | | |
|---|---|---|
| 3,905,108 | 9/1975 | Weiss et al. ........................ 433/173 |
| 4,215,986 | 8/1980 | Riess .................................. 433/173 |
| 4,854,872 | 8/1989 | Detsch ................................ 433/173 |
| 4,856,994 | 8/1989 | Lazzara et al. ...................... 433/173 |
| 4,872,839 | 10/1989 | Brajnovic ........................ 433/174 X |
| 4,988,297 | 1/1991 | Lazzara et al. ...................... 433/173 |

*Primary Examiner*—Robert P. Swiatek
*Assistant Examiner*—Elizabeth Shaw
*Attorney, Agent, or Firm*—Arnold, White & Durkee

[57] ABSTRACT

A gold abutment for receiving a cast metal substrate of an artificial tooth has a non-rotational (hexagonal) socket in its base. To prevent distorting the socket in the casting process the base is provided with an annular groove. Larger than usual base diameters can be used with no noticeable distortion of the socket.

40 Claims, 2 Drawing Sheets

THERMALLY STABILIZED CASTING CORE

This invention relates generally to cores on which to form articles from molten metal, more particularly to dental abutments made of precious metal, such as gold, on which artificial teeth, or substrates for artificial teeth, are cast. The invention is illustrated and described in connection with its use in implant dentistry.

BACKGROUND OF THE INVENTION

U.S. Pat. No.: 4,988,298 (which is owned by the Assignee of the present application) illustrates a popular technique for making artificial teeth intended to be installed directly on dental implants. A core in the form of an abutment base (10) which is attachable directly to a dental implant (30) supports a tooth substructure (52) covered with an anatomical overlay (58). The implant has a non-circular anti-rotation projection (34) and the base has a matching recess (22) dimensioned to fit snugly on the projection so that when the base is fitted to the implant relative rotation between them around their common axis will be prevented. A more generalized form of the core is shown in FIGS. 11A and 11B of U.S. Pat. No.: 4,955,811 (which also is owned by the Assignee of the present application). From these illustrations it will be seen that in general such cores comprise a base part containing a non-circular recess which mates with a projection on the implant, and has substantially the same external diameter as the implant where they mate, and a tubular, or "chimney" part of smaller diameter around which the tooth is formed. Where the two diameters meet the base part forms an annular shelf. In cases where the core is made of a precious metal and a metal substructure is cast to it, the molten metal comes in contact with the shelf and the chimney when the core is at a much lower temperature than the molten metal, subjecting the core to thermal shock. If the implant has a diameter in the range under about 3.75 mm. the difference in the two diameters is small enough so that such shock does not adversely affect the dimensions of the core, including the recess in its base part. However, recent developments have enabled the use of implants having wider diameters, in excess of 4 min. and up to about 8 mm. and more. U.S. Pat. No. 5,364,268 (owned by the Assignee of the present application) is illustratory. These developments have led in turn to new core designs having base parts with external diameters much larger than the chimney parts and consequently increased mass. When molten metal is cast to these new cores it is frequently found that the dimensions of the recess in the base part of the core are distorted so that the recess does not fit over the non-rotation projection of the implant on which the tooth is to be fitted. Bearing in mind that the dimensions of dental implants from any given manufacturer must be held to close standards and tolerances, and that some manufacturers of implants adhere to the same dimensional standards as others in order to enjoy interchangability with abutments made by others, it is important to find a solution to this problem.

GENERAL NATURE OF THE INVENTION

Applicants have found that if an annular groove is formed in the base part of a core made of metal (e.g: dental gold), after molten metal is cast to the core the dimensions and shape of the recess in the base are substantially unchanged from the dimensions and shape as they existed before the casting, when the core was at room temperature. In a preferred embodiment of the invention the groove opens through the shelf in the base part, surrounding the chimney part, and during the casting process the molten metal may flow into the groove. Applicants have found that with this improvement the anti-rotation recess in the base part of the core can continue to be made to the dimensional standards of many implant manufacturers and that those standards will be substantially intact after the casting process has been completed. The present invention relieves distortion of the recess which up to now has rendered the new core designs useless in practice.

The invention is described in greater detail with reference to the drawings that accompany this application. The scope of the invention is delineated in the claims appended to this specification.

DETAILED DESCRIPTION OF THE DRAWINGS

Figure 1:
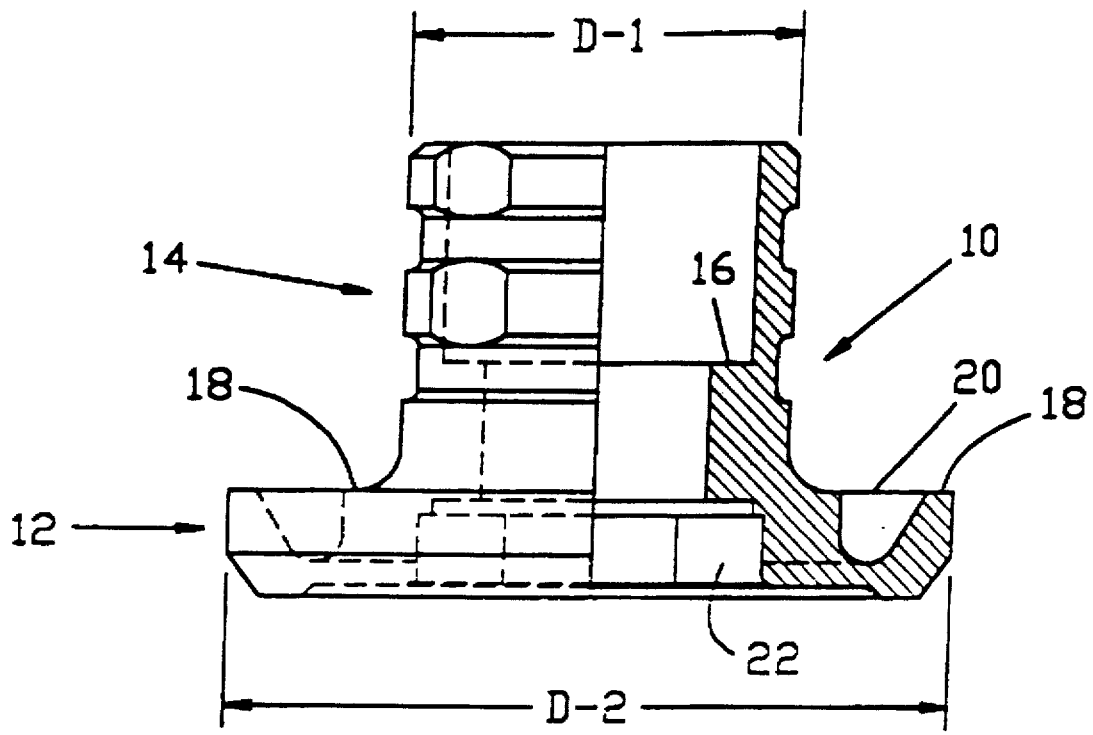
FIG. 1 is a side view of a preferred embodiment of an abutment according to the invention partially in longitudinal section.

The dental abutment 10 in FIG. 1 is made of a single piece of metal. For purposes of this description it is divided, conceptually, into a base part 12 and a chimney part 14. Compared to the abutments shown in the '298 and '811 patents referenced above the outer diameter D-2 of the base part is much larger than the outer diameter D-1 of the chimney part. In common with these prior-art abutments the chimney part 14 is tubular with an interior diameter that is reduced to form a shoulder 16, and the base part 12 has a hexagonal-form anti-rotation recess 22 opening through its bottom. An annular shelf 18 on the upper surface of the base part marks approximately the imaginary line of demarkation between the base and chimney parts. An annular groove 20 opening through the shelf 18 surrounds the chimney part.

Figure 1A:
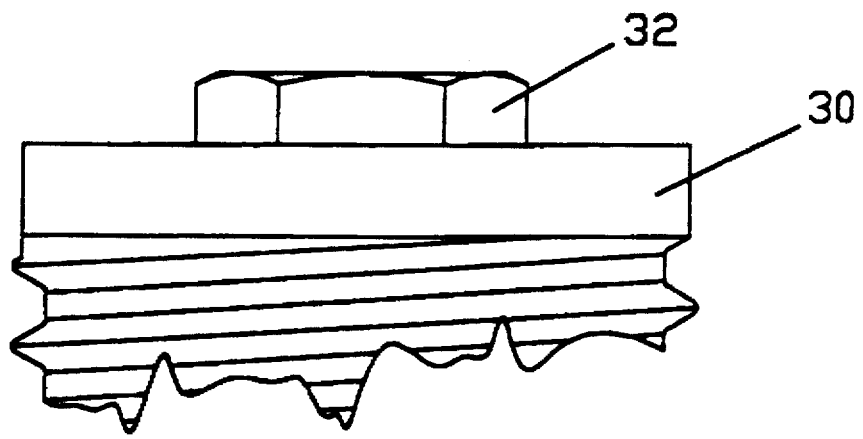
FIG. 1A schematically illustrates an implant positioned to mate with the abutment of FIG. 1.

FIG. 1A illustrates the top portion of an implant 30 with a hexagonal projection 32 of the kind intended for mating with the recess 22.

In the production of an artificial tooth on the abutment 10 it is the usual practice to form a "wax-up" of the shape to be formed on the abutment and then to form that shape of molten metal through the well-known "lost-wax" process. In that process molten metal is brought into contact with the outer surfaces of the abutment. This event rapidly raises the temperature of the abutment. As is explained above, prior experience has found that when the formed metal cools on the abutment the recess 22 fails to fit properly on the implant projection 32. This failure is substantially completely overcome with the groove 20.

Figure 2:
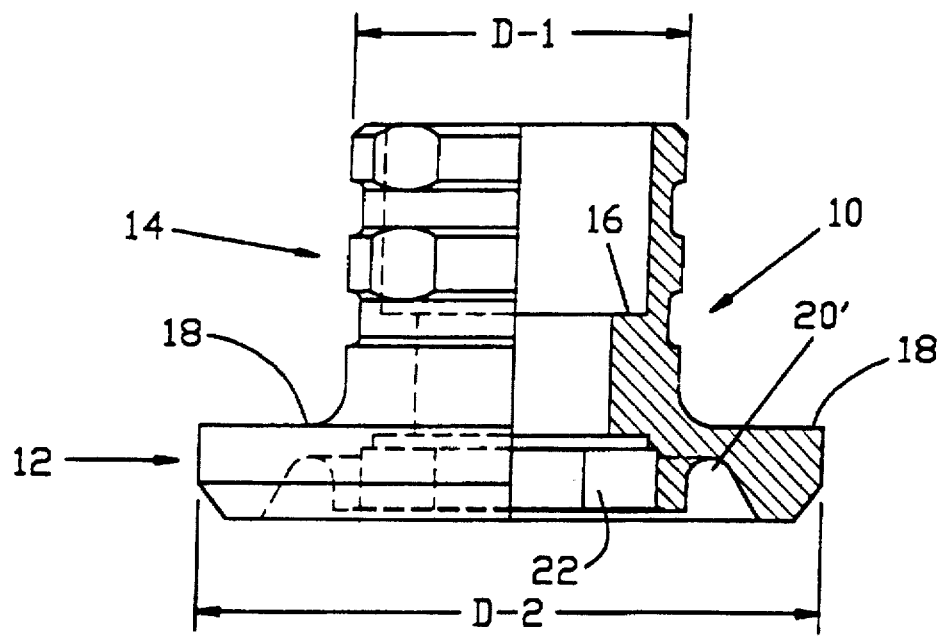
FIG. 2 is a similar view of another embodiment of the invention.

FIG. 2 differs from FIG. 1 in that the groove 20' opens through the bottom surface of the base part 12.

Figure 3:
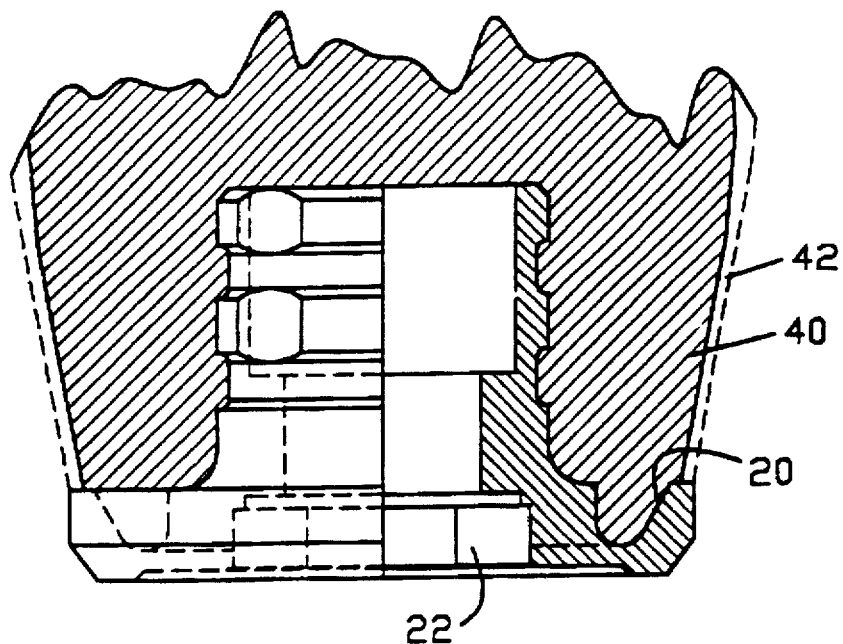
FIG. 3 shows an artificial tooth on the abutment of FIG. 1.

FIG. 3 shows an artificial tooth on an abutment according to FIG. 1. A metal substrate 40 in contact with the chimney part and the shelf is covered with an overlay 42 for replicating the appearance of a natural tooth. The metal of the substrate has entered the groove 20. It is found that the presence of the cast metal in the groove does not detract from the efficacy of the invention. The tooth thus made can be affixed to the implant as intended.

We claim:

1. A unitary core having a generally annular base part and a generally tubular mounting part arrayed endwise with a common passage through them, said core intended to support a body formed on its exterior from molten metal, said passage terminating in a recessed socket within said base part for connecting said core anti-rotationally to an implant, said base part having a larger external diameter than said mounting part, providing a substantially annular shelf extending radially outward relative to said mounting part in the vicinity of the junction betwen said two parts, and distortion relief means in said base part for minimizing shape distortion of said recessed socket resulting from contact with said molten metal.

2. A core according to claim 1 in which said distortion relief means is substantially a groove.

3. A core according to claim 2 in which said groove opens through said shelf.

4. A core according to claim 2 in which said groove is axially oriented.

5. A core according to claim 4 and said body formed on it in contact with said mounting part and said shelf and substantially filling said groove.

6. A core according to claim 2 in which said distortion relief means is a substantially continuous annular groove.

7. A core according to claim 6 in which said groove is axially oriented.

8. A core according to claim 6 in which said groove opens through said shelf.

9. A core according to claim 8 and said body formed on it in contact with said mounting part and said shelf and substantially filling said groove.

10. A core according to claim 1 in which said passage terminates through said base in a socket for matingly engaging another article so as to attach said core to said other article.

11. A core according to claim 10 including means to affix said core to said other article.

12. A core according to claim 1 and said body formed on it in contact with said mounting part and said shelf.

13. A unitary core having a generally annular base part and a generally tubular mounting part arrayed endwise with a common passage through them, said passage terminating through said base in a socket for matingly engaging another article so as to attach said core to said other article, said socket having a non-round shape transverse to said passage, said core intended to support a body formed on its exterior from molten metal, said base part having a larger external diameter than said mounting part, providing a substantially annular shelf extending radially outward relative to said mounting part in the vicinity of the junction betwen said two parts, and distortion relief means in said base part for minimizing shape distortion of said base part resulting from contact with said molten metal.

14. In combination, a core and a body cast on the exterior of said core from molten metal, said core having a generally annular shape and a recessed socket at one end for engaging an implant, said core including distortion relief means at said one end for minimizing shape distortion of said socket resulting from contact with said molten metal.

15. The combination of claim 14 wherein said distortion relief means is substantially a groove and wherein said body formed on the exterior of said core substantially fills said groove.

16. A core of generally annular shape having in one end a recessed socket for engaging another article, said core intended to support a body formed on its exterior from molten metal, said core having a passage through it from one end to the other and including distortion relief means for minimizing shape distortion of said socket resulting from contact with said molten metal.

17. A core according to claim 16 in which said passage terminates in said socket.

18. A core according to claim 17 in which said socket has a non-round shape transverse to said passage.

19. A core according to claim 17 including means operable through said passage for affixing said core to said other article.

20. A generally tube-shaped unitary dental core on which to form an artificial tooth including a metallic substrate formed in place from the molten state on an exterior surface thereof, said core being of generally annular shape having in one end a recessed socket for engaging an implant, and including means for minimizing shape distortion of said socket due to contact with said metal in said molten state.

21. A core according to claim 20 in which the mass of said core is reduced near said one end to minimize said distortion.

22. A core according to claim 20 in which said distortion minimizing means comprises a groove in said core near said one end.

23. A core according to claim 22 in which said groove is a substantially continuous annular groove.

24. A generally tube-shaped unitary dental core on which to form an artificial tooth including a metallic substrate formed in place from the molten state on an exterior surface thereof, said core having a passage through it from one end to the other and being of generally annular shape having in one end a recessed socket for engaging another article, and including means for minimizing shape distortion of said socket due to contact with said metal in said molten state.

25. A core according to claim 24 in which said one end is widened to a larger diameter than said other end and provides a substantially annular shelf extending radially outward relative to said socket.

26. A core according to claim 25 in which said distortion minimizing means comprises a groove opening through said shelf.

27. A core according to claim 25 and said substrate formed on it in contact with said core and said shelf.

28. A core according to claim 27 in which said distortion minimizing means comprises a groove through said shelf and said substrate substantially fills said groove.

29. A core according to claim 25 in which said larger diameter is not less than about 4 mm.

30. A core according to claim 29 in which said larger diameter is at least about 6 mm.

31. A core according to claim 24 in which said passage terminates in said socket.

32. A core according to claim 31 in which said socket has a non-round shape transverse to said passage.

33. A core according to claim 31 including means operable through said passage for affixing said core to said other article.

34. In combination, a core according to claim 31 and a dental implant having coupling means for cooperating with said socket, and means to affix said core to said implant.

35. A combination according to claim 34 in which said second part of said core and said implant have substantially round meeting surfaces which have substantially the same diameter not smaller than about 4 mm.

36. A combination according to claim 35 in which said diameter is at least about 6 mm.

37. A combination according to claim 36 in which the largest transverse dimension of said socket is about 45% of said diameter.

38. In combination, a generally tube-shaped unitary dental core on which to form an artificial tooth including a metallic substrate formed in place from the molten state on an exterior surface thereof, said core being of generally annular shape having in one end a recessed socket for engaging another article, and including means for minimizing shape distortion of said socket due to contact with said metal in said molten state, an artificial tooth on said core, a dental implant, and means to affix said core to said implant.

39. A combination according to claim 38 in which said implant has a diameter not smaller than about 4 mm.

40. A combination according to claim 39 in which said diameter is at least 5 mm.

* * * * *